US00PP35767P2

(12) United States Plant Patent
Koppe

(10) Patent No.: US PP35,767 P2
(45) Date of Patent: Apr. 23, 2024

(54) ***BEGONIA* PLANT NAMED 'KRMOCOR01'**

(50) Latin Name: ***Begonia* x *hiemalis***
Varietal Denomination: KRMOCOR01

(71) Applicant: KOPPE ROYALTY B.V., Putten (NL)

(72) Inventor: Lubbertus H. Koppe, Putten (NL)

(73) Assignee: KOPPE ROYALTY B.V., Putten (NL)

( * ) Notice: Subject to any disclaimer, the term of this patent is extended or adjusted under 35 U.S.C. 154(b) by 0 days.

(21) Appl. No.: 18/226,196

(22) Filed: Jul. 25, 2023

(51) Int. Cl.
*A01H 5/02* (2018.01)
*A01H 6/18* (2018.01)

(52) U.S. Cl.
USPC ..... Plt./347

(58) Field of Classification Search
USPC ..... Plt./344, 347
See application file for complete search history.

*Primary Examiner* — Susan McCormick Ewoldt
(74) *Attorney, Agent, or Firm* — C. Anne Whealy

(57) ABSTRACT

A new and distinct cultivar of *Begonia* plant named 'KRMOCOR01' characterized by its broadly upright to spreading and mounded plant habit; moderately vigorous growth habit; moderately freely branching habit; dark green-colored leaves; freely flowering habit; double-type male and single-type female flowers that are red orange in color and held above and beyond the foliar plane; and good postproduction longevity.

2 Drawing Sheets

Figure 1:
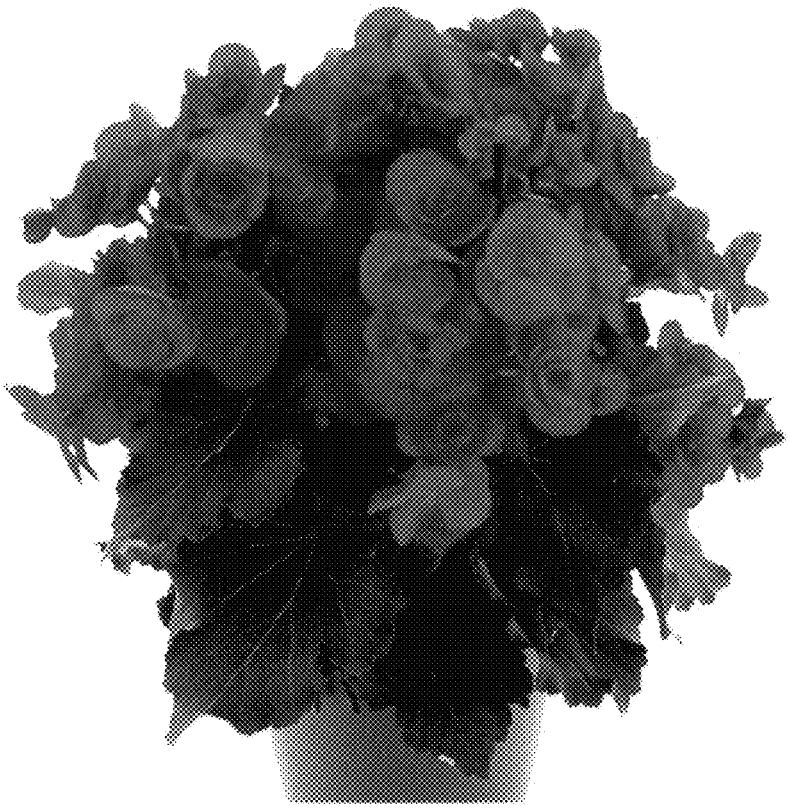

Botanical designation: *Begonia* x *hiemalis*.
Cultivar denomination: 'KRMOCOR01'.

PRIOR DISCLOSURES BY THE INVENTOR & APPLICANT/ASSIGNEE

An European Community Plant Breeder's Rights application for the instant plant was filed by the Applicant/Assignee, Koppe Royalty B.V. of Putten, The Netherlands on Nov. 11, 2022, application number 2022/2525. Foreign priority is not claimed to this application.

BACKGROUND OF THE INVENTION

The present invention relates to a new and distinct cultivar of *Begonia* plant, botanically known as *Begonia* x *hiemalis*, commercially referred to as an Elatior *Begonia* and hereinafter referred to by the name 'KRMOCOR01'.

The new *Begonia* plant is a product of a planned breeding program conducted by the Inventor in Ermelo, The Netherlands. The objective of the breeding program is to create new freely-branching and freely-flowering *Begonia* plants with attractive flower color and excellent postproduction longevity.

The new *Begonia* plant originated from a cross-pollination made by the Inventor in December, 2017 of a proprietary selection of *Begonia* x *tuberhybrida* identified as code number KV15K2158-022, not patented, as the female, or seed, parent with a proprietary selection of *Begonia socotrana* identified as code number S00, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in June, 2019.

Asexual reproduction of the new *Begonia* plant by terminal vegetative cuttings taken in a controlled greenhouse environment in Ermelo, The Netherlands since December, 2019 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRMOCOR01'. These characteristics in combination distinguish 'KRMOCOR01' as a new and distinct *Begonia* plant:

1. Broadly upright to spreading and mounded plant habit.
2. Moderately vigorous growth habit.
3. Moderately freely branching habit.
4. Dark green-colored leaves.
5. Freely flowering habit.
6. Double-type male and single-type female flowers that are red orange in color and held above and beyond the foliar plane.
7. Good postproduction longevity.

Plants of the new *Begonia* differ primarily from plants of the female parent selection in flower form as male flowers of plants of the new *Begonia* are double-types whereas male flowers of plants of the female parent selection are single-types.

Plants of the new *Begonia* differ primarily from plants of the male parent selection in flower form as male flowers of plants of the new *Begonia* are double-types whereas male flowers of plants of the male parent selection are single-types. In addition, flowers of plants of the new *Begonia* are red orange in color whereas flowers of plants of the male parent selection are purplish pink in color.

Plants of the new *Begonia* can be compared to plants of *Begonia* x *hiemalis* 'Reina', disclosed in U.S. Plant Pat. No. 19,336. In side-by-side comparisons, plants of the new *Begonia* differ primarily from plants of 'Reina' in leaf color as plants of the new *Begonia* have darker green-colored leaves than plants of 'Reina'. In addition, plants of the new *Begonia* differ from plants of 'Reina' in flower color as plants of the new *Begonia* have darker red orange-colored flowers than plants of 'Reina'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1) is a side perspective view of a typical plant of 'KRMOCOR01' grown in a container.

Figure 2:
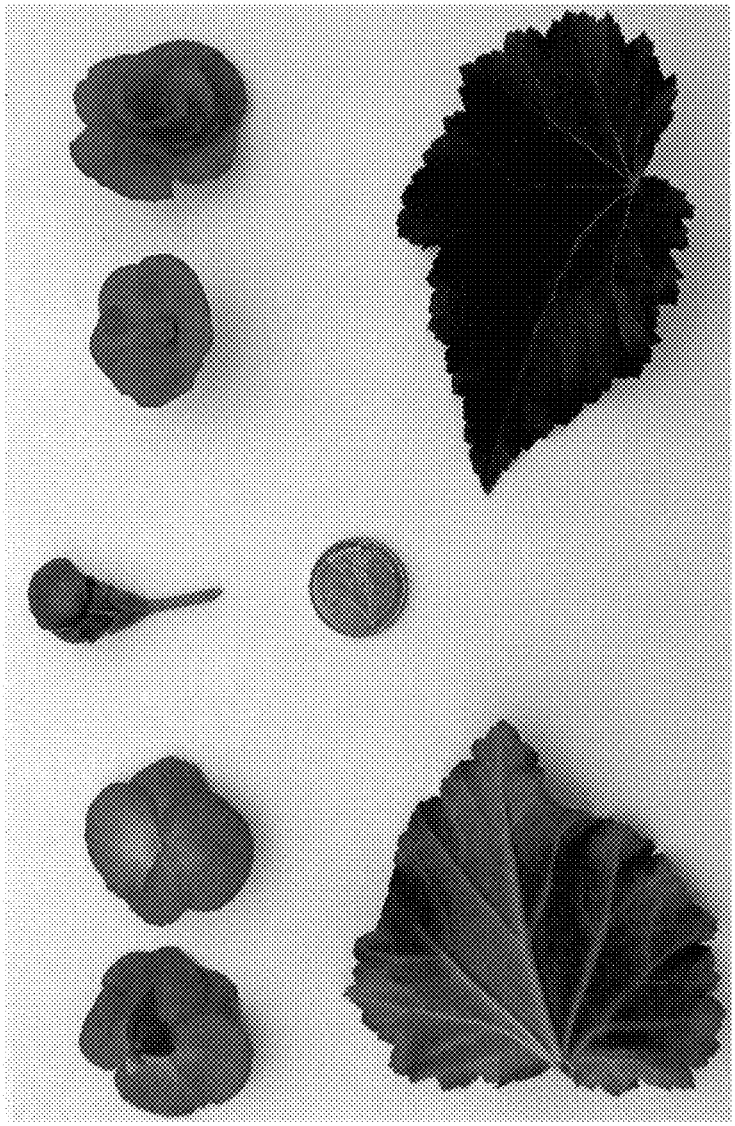

The photograph on the second sheet (FIG. 2) are close up views of the upper (right) and lower (left) surfaces of typical leaves and flowers of 'KRMOCOR01'.

At the top of second sheet, from left to right, are close up views of a typical double male flower, a typical single female flower, a typical flower bud, a typical single female flower and a typical double male flower.

DETAILED BOTANICAL DESCRIPTION

The aforementioned photographs and following observations and measurements describe plants grown during the summer in 13-cm containers in a glass-covered greenhouse in Ermelo, The Netherlands and under cultural practices typical of commercial *Begonia* production. During the production of the plants, day temperatures ranged from 20 C to 22 C and night temperatures ranged from 16 C to 18 C. Plants were three months old when the photographs and description were taken. In the following description, color references are made to The Royal Horticultural Society Colour Chart, 2015 Edition, except where general terms of ordinary dictionary significance are used.

Botanical classification: *Begonia* x *hiemalis* 'KRMOCOR01'.

Parentage:

*Female, or seed, parent*.—Proprietary selection of *Begonia* x *tuberhybrida* identified as code number KV15K2158-022, not patented.

*Male, or pollen, parent*.—Proprietary selection of *Begonia socotrana* identified as code number S00, not patented.

Propagation:

*Type*.—By terminal vegetative cuttings.

*Time to initiate roots, summer and winter*.—About 20 days at temperatures about 20 C.

*Time to produce a rooted young plant, summer and winter*.—About five weeks at temperatures about 20 C.

*Root description*.—Fine, fibrous; typically white to orangish brown in color, actual color of the roots is dependent on substrate composition, water quality, fertilizer type and formulation, substrate temperature and physiological age of roots.

*Rooting habit*.—Freely branching; medium density; to date, plants of the new *Begonia* have not been observed to form tubers.

Plant description:

*Plant habit and form*.—Broadly upright to spreading and mounded plant habit; broadly oblong to close to spherical in overall plant shape.

*Growth habit*.—Moderately vigorous growth habit and moderate growth rate; suitable for 9-cm and larger containers; under optimal environmental and cultural conditions, usually about eleven weeks from rooted cuttings are required to produce proportional plants in 13-cm containers.

*Branching habit*.—Moderately freely branching with about four primary branches each with about three secondary branches developing per plant.

*Plant height, soil level to top of foliar plane*.—About 23.8 cm.

*Plant height, soil level to top of floral plane*.—About 26.6 cm.

*Plant width*.—About 35.7 cm.

*Lateral branches*.—Length: About 13.8 cm. Diameter: About 1 cm. Internode length: About 2.8 cm. Strength: Moderately strong. Aspect: Erect to about 50 degrees from vertical. Texture and luster: Sparsely pubescent; slightly glossy. Color, developing: Close to 152B. Color, developed: Close to a blend of 146A and 152A; surfaces exposed to sunlight are tinged with close to N170B; at the internodes, close to 146A. Lenticels: Quantity: Sparse. Length: About 2 mm. Width: About 0.75 mm. Shape: Linear. Color: Close to 145B.

*Leaves*.—Arrangement: Alternate, simple. Length: About 14.7 cm. Width: About 10.8 cm. Shape: Unequal broadly ovate. Apex: Acute to minutely apiculate. Base: Oblique, lobes free to imbricate. Margin: Crenate to dentate; moderately undulate. Texture and luster, upper surface: Sparsely pubescent; velvety; slightly glossy. Texture and luster, lower surface: Mostly smooth and glabrous with sparse pubescence along the venation; velvety; moderately glossy to glossy. Venation pattern: Pinnate. Color: Developing leaves, upper surface: Close to a blend of N199A and N199B. Developing leaves, lower surface: Close to 182A. Fully expanded leaves, upper surface: Close to a blend of N189A and 203A; venation, close to 146A. Fully expanded leaves, lower surface: Close to 183C; venation, close to 148A. Petioles: Length: About 4.9 cm. Diameter: About 6 mm. Strength: Low, flexible. Texture and luster, upper and lower surfaces: Sparsely pubescent; moderately glossy. Color, upper surface: Close to 146B; distally, strongly tinged with close to 183A and 183B. Color, lower surface: Close to 146C; distally, strongly tinged with close to 183A and 183B. Stipules: Quantity and appearance: Two leafy stipules at the base of each leaf. Length: About 9 mm. Width: About 1.1 cm. Shape: Broadly ovate to close to deltoid. Apex: Broadly acute. Base: Broadly cuneate. Margin: Finely ciliate. Color, upper and lower surfaces: Close to 146D; towards the margins and apex, close to 181D; venation, close to 181D.

Flower description:

*Flower form and flowering habit*.—Double-type male and single-type female rotate flowers arranged in axillary cymes; typically about eight flowers per cyme, numerous cymes in flower simultaneously and about 560 male and 80 female flowers developing per plant; flowers face upright to outwardly and are positioned above and beyond the foliar plane.

*Natural flowering season*.—Plants flower continuously from the spring into the autumn in The Netherlands.

*Flower longevity*.—Individual flowers last about two weeks on the plant; flowers not persistent.

*Fragrance*.—None detected.

*Inflorescence height*.—About 16.8 cm.

*Inflorescence diameter*.—About 8.7 cm.

*Flower buds, male flowers*.—Length: About 8 mm. Diameter: Ranging from about 5 mm to 14 mm. Shape: Reniform, flattened. Texture and luster: Smooth, glabrous; slightly velvety; matte. Color: Close to 45D; towards the base, close to 39D.

*Flower buds, female flowers*.—Length: About 9 mm. Diameter: About 7 mm. Shape: Ovate. Texture and luster: Smooth, glabrous; slightly velvety; matte. Color: Close to 45D; towards the base, close to 39D.

*Male flowers*.—Diameter: About 5.1 cm. Depth: About 2.2 cm. Shape and type: Rotate; double. Tepals: Quantity and arrangement: About four arranged in two whorls. Length, outer whorl tepals: About 2.9 cm. Length, inner whorl tepals: About 2.6 cm. Width, outer whorl tepals: About 3.5 cm. Width, inner whorl tepals: About 2.6 cm. Shape, all tepals: Reniform to roughly orbicular. Apex, all tepals: Mostly rounded. Base, outer whorl tepals: Truncate. Base, inner whorl tepals: Cuneate. Margin, all tepals: Entire, not undulate. Texture and luster, upper surface, all tepals: Smooth, glabrous; velvety; matte. Texture and luster, lower surface, all tepals: Smooth, glabrous; velvety; slightly glossy to matte. Color, outer whorl tepals: When opening, upper surface: Close to N34B. When opening, lower surface: Close to 39A; towards the base, close to 39B. Fully opened, upper surface: Close to 33A; towards the base, close to 34B; venation, close to 34A; color does not change with subsequent development. Fully opened, lower surface: Close to 45C and 45D; venation, close to N34C; color does not change with subsequent development. Color, inner whorl tepals: When opening, upper surface: Close to a blend of N34B and 40B. When opening, lower surface: Close to 39A. Fully opened, upper surface: Close to 33A; towards the base, close to 33B; venation, close to 34A; color does not change with subsequent development. Fully opened, lower surface: Close to 43C; towards the base, close to 43D; venation, close to N34C; color does not change with subsequent development.

*Female flowers*.—Diameter: About 5.2 cm. Depth: About 2.7 cm. Shape and type: Rotate; single. Tepals: Quantity and arrangement: About five to occasionally six arranged in two whorls. Length: About 2.6 cm. Width: About 3.2 cm. Shape: Reniform to roughly orbicular. Apex: Mostly rounded. Base: Cuneate. Margin: Entire, not undulate. Texture and luster, upper and lower surfaces: Smooth, glabrous; velvety; matte. Color: When opening, upper surface: Close to 33A. When opening, lower surface: Close to 45C; towards the base, close to 45D. Fully opened, upper surface: Close to N30A; towards the base, close to N30B; venation, similar to lamina color; color does not change with subsequent development. Fully opened, lower surface: Close to 41B; venation, close to N34C; color does not change with subsequent development. Tepaloids: Quantity and arrangement per flower: About 15 to 19 per male flower arranged in about four whorls. Length: About 7 mm to 22 mm. Width: About 3 mm to 17 mm. Shape: Obovate. Apex: Obtuse to broadly retuse. Base: Cuneate. Margin: Entire; not undulate. Texture and luster, upper and lower surfaces: Smooth, glabrous; velvety; matte. Color: When opening, upper surface: Close to 40A. When opening, lower surface: Close to 43B; towards the base, close to 43D. Fully opened, upper surface: Close to 40A; towards the base, close to 33B; venation, close to 34A; color does not change with subsequent development. Fully opened, lower surface: Close to 44C; towards the base, close to 43C; venation, close to N34C; color does not change with subsequent development.

*Flower bracts*.—Quantity and arrangement: Two positioned at the top of the peduncle. Length: About 1.2 cm. Width: About 1.5 cm. Shape: Reniform. Apex: Broadly obtuse. Base: Broadly cuneate. Margin: Finely ciliate. Texture and luster, upper and lower surfaces: Smooth, glabrous; moderately velvety; slightly glossy. Color, upper and lower surfaces: Translucent, close to 143C; venation, close to 175B.

*Peduncles*.—Length: About 11.5 cm. Diameter: About 4 mm to 5 mm. Strength: Moderately strong. Aspect: About 30 degrees from lateral branch axis. Texture and luster: Smooth and glabrous to sparsely pubescent; moderately glossy. Color: Close to 152A.

*Pedicels*.—Length: About 2.3 cm. Diameter: About 2 mm. Strength: Moderately strong. Aspect: About 30 degrees from peduncle axis. Texture and luster: Smooth, glabrous; glossy. Color: Close to 172B.

*Reproductive organs*.—Stamens: To date, no female flower development has been observed on plants of the new *Begonia*. Pistils (present on female flowers only): Quantity of pistils per flower: Three. Pistil length: About 5 mm. Style length: About 4 mm. Style color: Close to 30A. Stigma diameter: About 4 mm. Stigma shape: Cleft, spiral. Stigma color: Close to 17A. Ovary color: Close to 144A and 144B. Seeds and fruits: To date, seed and fruit development have not been observed on plants of the new *Begonia*.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures about 35 C and to be suitable for USDA Hardiness Zones 10 to 12.

It is claimed:

1. A new and distinct *Begonia* plant named 'KRMOCOR01' as illustrated and described.

* * * * *